US012768923B2

(12) United States Patent
Hoshino

(10) Patent No.: US 12,768,923 B2
(45) Date of Patent: Oct. 20, 2026

(54) MAGNETIC RESONANCE IMAGING APPARATUS AND METHOD OF CONTROLLING THE SAME

(71) Applicant: FUJIFILM Corporation, Tokyo (JP)

(72) Inventor: Yusuke Hoshino, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/300,447

(22) Filed: Aug. 14, 2025

(65) Prior Publication Data

US 2026/0056275 A1 Feb. 26, 2026

(30) Foreign Application Priority Data

Aug. 21, 2024 (JP) ................................ 2024-140063

(51) Int. Cl.
*A61B 5/00* (2006.01)
*A61B 5/055* (2006.01)
*G01R 33/56* (2006.01)
*G01R 33/565* (2006.01)

(52) U.S. Cl.
CPC ........ *G01R 33/56509* (2013.01); *A61B 5/055* (2013.01); *A61B 5/721* (2013.01); *A61B 5/7285* (2013.01); *G01R 33/5608* (2013.01); *A61B 2576/00* (2013.01)

(58) Field of Classification Search
CPC .......... G01R 33/56509; G01R 33/5608; G01R 33/543; G01R 33/5673; G01R 33/5676; G01R 33/567; A61B 5/055; A61B 5/721; A61B 5/7285; A61B 2576/00
See application file for complete search history.

(56) References Cited

U.S. PATENT DOCUMENTS

| | | | | |
|---|---|---|---|---|
| 11,927,658 B2 * | 3/2024 | Shoji | | G01R 33/4818 |
| 2020/0205748 A1 | 7/2020 | Pautsch et al. | | |
| 2023/0045497 A1 * | 2/2023 | Shoji | | G01R 33/5611 |
| 2024/0264258 A1 * | 8/2024 | Shoji | | A61B 5/0059 |

FOREIGN PATENT DOCUMENTS

| | | |
|---|---|---|
| JP | 2023-022669 A | 2/2023 |
| JP | 7242514 B2 | 3/2023 |

OTHER PUBLICATIONS

Extended European Search Report issued in EP 25197319.4-1122 by the European Patent Office on Jan. 19, 2026.

* cited by examiner

*Primary Examiner* — Joel Lamprecht
(74) *Attorney, Agent, or Firm* — Studebaker Brackett PLLC

(57) ABSTRACT

The present invention aims to, in a case where measurement data affected by a body movement that occurred during an examination is re-measured, reduce a time extension caused by the re-measurement.

Whether or not re-measurement is necessary is determined in consideration of continuity of measurement data affected by a body movement. In addition, in a case of performing the re-measurement, measurement of a part of unmeasured measurement data is omitted in consideration of a measurement time (number of phase encoding steps) of the measurement data to be re-measured.

11 Claims, 10 Drawing Sheets

MAGNETIC RESONANCE IMAGING APPARATUS AND METHOD OF CONTROLLING THE SAME

CROSS-REFERENCE TO RELATED APPLICATIONS

The present application claims priority under 35 U.S. C. § 119 to Japanese Patent Application No. 2024-140063, filed Aug. 21, 2024. Each of the above application(s) is hereby expressly incorporated by reference, in its entirety, into the present application.

BACKGROUND OF THE INVENTION

1. Field of the Invention

The present invention relates to a magnetic resonance imaging apparatus (hereinafter, referred to as an MRI apparatus), and particularly relates to processing of measurement data in a case where a body movement of a subject occurs during an examination using the MRI apparatus.

2. Description of the Related Art

In the examination using the MRI apparatus, the subject is placed in an imaging space in which a static magnetic field is generated, and imaging is performed by repeatedly applying a radio-frequency magnetic field pulse and a gradient magnetic field pulse according to a predetermined pulse sequence. In a case where the subject moves during the imaging, body movement artifacts are generated in an image using measurement data obtained by the imaging.

Therefore, in the related art, the movement of the subject during the examination is monitored, and in a case where the measurement data being acquired is affected by the body movement, the data (hereinafter, referred to as body movement-affected data) is specified, the body movement-affected data is deleted or corrected to perform image reconstruction, or the body movement-affected data is re-taken in a case where the correction is not sufficient.

For example, JP07242514B discloses a technique of monitoring a movement of a patient by using an image sensor installed in an imaging bore, and taking an appropriate action based on a location where the detected body movement occurs or a level of the body movement. This technique discloses appropriate actions such as pausing a scan until the movement stops and annotating data frames acquired during the movement.

In addition, JP2023-022669A discloses a technique of analyzing a body movement of a subject and determining, depending on characteristics of the body movement, whether or not subsequent processing, that is, body movement correction is necessary and whether or not re-measurement is necessary. Further, JP2023-022669A discloses that, in a case of excluding body movement-affected data in the body movement correction, a thinning-out rate of the entire measurement data is considered, and a restriction is imposed on the data to be excluded depending on a region of a k-space.

SUMMARY OF THE INVENTION

According to the technique in the related art, for example, the technique disclosed in JP2023-022669A, it is possible to obtain an image in which the effects of the body movement are reduced without degrading the image quality by determining whether or not the re-measurement is necessary depending on the characteristics of the body movement. However, in a case where the body movement-affected data is excluded or re-measured while maintaining the image quality, there is a problem in that an imaging time is prolonged. For example, there are various aspects of the body movement, such as a relatively continuous body movement or a body movement that occurs frequently in a short time. In a case where the determination to re-take (re-measure) the body movement-affected data is made only on the basis of the magnitude of the body movement and the position of the body movement-affected data in the k-space, there is a possibility that the re-measurement has to be repeatedly performed, and the imaging time is prolonged. In addition, in a case of determining whether or not the re-measurement is necessary based on a proportion of the body movement-affected data in the k-space, the determination as to whether or not the re-measurement is necessary is made after collection of the measurement data of a certain proportion, and there is a possibility that the re-measurement is performed even on data for which the re-measurement is not necessary, which inevitably results in extension in imaging time.

An object of the present embodiment is to provide a technique capable of obtaining an image in which the effects of the body movement are reduced while avoiding extension in imaging time required to perform the re-measurement to re-take the body movement-affected data as much as possible.

In the present invention, for the necessity of the re-measurement and conditions for the re-measurement, a determination criterion is provided for the position of the body movement-affected data in the k-space, in particular, the position or continuity in a case where the body movement-affected data is in a high frequency region in the k-space, and the determination criterion is applied to the body movement-affected data to determine subsequent processing. This allows for optimization of the processing and reduces the measurement time required for the re-measurement.

That is, an MRI apparatus according to an aspect of the present invention comprises: an imaging unit that collects nuclear magnetic resonance signals of a subject; an image generation unit that reconstructs an image of the subject using k-space data consisting of the nuclear magnetic resonance signals collected by the imaging unit; a body movement processing unit that analyzes a body movement of the subject during imaging and that specifies body movement-affected data that is affected by the body movement of the subject among the k-space data; and a processor that controls the imaging unit and the image generation unit. The processor determines whether to subject the body movement-affected data to body movement correction reconstruction or to re-measure the body movement-affected data according to a position of the body movement-affected data in a k-space and the number of consecutive data points of the body movement-affected data, and, in a case where it is determined to re-measure at least a part of the body movement-affected data, the processor controls the imaging unit to execute the re-measurement.

In addition, a method of controlling an MRI apparatus according to another aspect of the present invention includes the following steps.

The method comprises: a step of specifying body movement-affected data affected by a body movement, which is included in k-space data collected by the MRI apparatus; a step of determining whether or not re-measurement of the body movement-affected data is necessary, based on a position of the body movement-affected data in a k-space; a step of, in a case where it is determined that the re-measurement is not necessary, further determining whether or not re-measurement of the body movement-affected data is necessary, based on the number of consecutive data points of the body movement-affected data; and a step of, in a case where it is determined that re-measurement of at least a part of the body movement-affected data is necessary, setting a condition for the re-measurement.

According to the present invention, it is possible to minimize the number of data to be re-measured and to reduce the measurement time while maintaining the image quality of the image after the body movement correction by determining whether or not the re-measurement is necessary or adjusting the conditions for the re-measurement in consideration of the continuity of the body movement-affected data.

DESCRIPTION OF THE PREFERRED EMBODIMENTS

First, an outline of an MRI apparatus to which the present invention is applied will be described with reference to FIG. 1.

Figure 1:
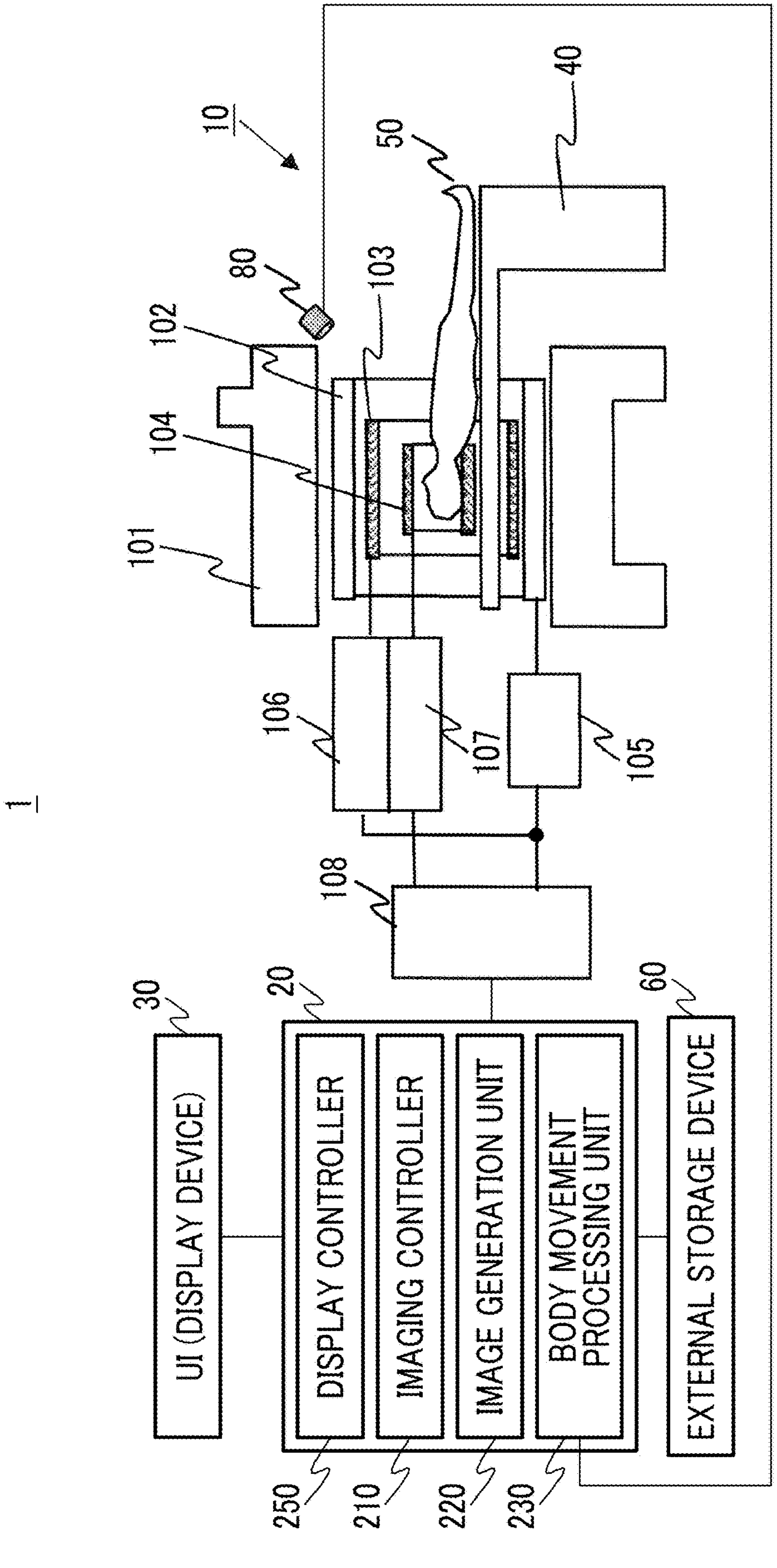
FIG. 1 is a diagram showing an overall outline of an MRI apparatus.

As shown in FIG. 1, an MRI apparatus 1 is roughly divided into an imaging unit 10, a processor 20 that performs various controls and calculations, and a user interface (UI) unit 30 that allows communication between the imaging unit 10 and the processor 20 and a user. Main elements constituting the imaging unit 10 are housed in a gantry that provides an examination space.

The imaging unit 10 induces nuclear magnetic resonance in nuclei (usually protons) of atoms that constitute a tissue of a subject, and collects nuclear magnetic resonance signals (NMR signals) generated by the resonance from the subject. Hereinafter, the nuclear magnetic resonance signal is also simply referred to as a measurement signal or an echo signal.

A configuration of the imaging unit 10 is similar to that of a known MRI apparatus, and comprises a static magnetic field magnet 101 that generates a uniform magnetic field (static magnetic field) in the examination space in which a subject 50 is placed, a gradient magnetic field coil 102 that applies a gradient magnetic field to the static magnetic field, an RF transmission coil 103 that applies a radio-frequency magnetic field to excite the nuclei of the atoms constituting the tissue of the subject, and an RF receive coil 104 that receives the NMR signal generated by the subject, in which the gradient magnetic field coil 102, the RF transmission coil 103, and the RF receive coil 104 are connected to a gradient magnetic field power supply 105, a transmitter 106, and a receiver 107, respectively. Operations of the gradient magnetic field power supply 105, the transmitter 106, and the receiver 107 are controlled by a sequencer 108. The sequencer 108 determines a pulse sequence for each scan using a set pulse sequence type and imaging conditions such as imaging parameters, and controls each component of the imaging unit 10 to operate in accordance with the determined pulse sequence and collect an echo signal (k-space data) necessary for image reconstruction. Since functions and operations of each component in a case where the imaging unit 10 collects the k-space data are similar to those of a general MRI apparatus, detailed description thereof will be omitted here.

The static magnetic field magnet 101, the gradient magnetic field coil 102, and the RF transmission coil 103 are housed in the gantry, and the subject 50 is positioned in the examination space in the gantry in a state of being laid on a bed device 40 with the RF receive coil 104 attached to an examination part.

The processor 20 is a device that performs control and calculation of the device, and can be configured as a known processing device such as a computer comprising a CPU and a memory, a programmable IC, or a combination thereof. In a case of a computer, the processing of the processor is realized by the CPU reading a program that achieves each function of control or calculation. In addition, all of the functions of the processor can be realized by a single processor, but each function can also be realized by a combination of one or a plurality of processors. In FIG. 1, one processor 20 represents one or a plurality of processors, and individual functions realized by one or a plurality of processors 20 are shown.

In the example of FIG. 1, the processor 20 comprises an imaging controller 210 that controls the operation of the imaging unit 10, an image generation unit 220 that generates an image of the subject using the echo signal collected by the imaging unit 10, a body movement processing unit 230 that performs processing related to the body movement of the subject 50 during the examination, and a display controller 250 that controls a GUI for displaying the image generated by the image generation unit 220 and for interacting with the user. FIG. 1 illustrates typical functions of the processor 20 of the present embodiment, and each function does not necessarily correspond to an individual processor or processing unit. In some cases, one processor or processing unit realizes functions of a plurality of functional units, or a plurality of processors or a plurality of processing units realize one function.

The imaging controller 210 controls the imaging unit 10 via the sequencer 108 that operates each element of the imaging unit 10 in accordance with a predetermined pulse sequence. The sequencer 108 operates each component of the imaging unit 10 based on imaging conditions such as a pulse sequence and a scan parameter, which are determined by an examination flow or set by the user. In a case where the body movement processing unit 230 described below collects body movement information from echo signals (navigator echoes) for body movement detection, the imaging controller 210 executes a sequence for collecting the navigator echoes together with a pulse sequence for an image or by incorporating the sequence for collecting the navigator echoes into the pulse sequence for an image. In addition, the imaging controller 210 performs control of stopping or resuming the imaging according to the body movement analyzed by the body movement processing unit 230, and performs control of re-measurement for re-taking a part of the k-space data affected by the body movement.

The image generation unit 220 performs calculations necessary for image reconstruction, such as Fourier transform and sequential calculations, on the k-space data collected by the imaging unit 10, and performs calculations such as correction on the k-space data before reconstruction or the image after reconstruction. In the present embodiment, image reconstruction (body movement-corrected reconstruction) in which the body movement is corrected is performed according to the body movement analyzed by the body movement processing unit 230. In addition, in a case where a part of the k-space data is re-measured by the imaging unit 10, the k-space data obtained by the re-measurement and the k-space data obtained before the re-measurement may be combined to perform image reconstruction.

The body movement processing unit 230 collects and processes the body movement information occurring in the subject 50 during the examination, for example, information related to a size and a duration of the body movement, and particularly, the number of consecutive data points, and associates the body movement information with the ongoing scan (imaging) to determine whether or not body movement correction is necessary and whether or not re-measurement is necessary. The body movement information can be acquired from body movement detection means such as a surveillance camera 80 for monitoring the movement of the subject 50 and a navigator echo for detecting the movement of the subject. Although one surveillance camera 80 is illustrated in FIG. 1 as a representative, one or a plurality of surveillance cameras 80 are installed in the vicinity or inside of the gantry, acquire a video of the examination space, and transmit the video to the processor 20 (body movement processing unit 230). As described above, the navigator echo is a nuclear magnetic resonance signal collected to detect the movement of the subject, separately from the nuclear magnetic resonance signal (echo signal) for the imaging unit 10 to generate the image of the subject, and the body movement processing unit 230 extracts the movement of the subject at the time of imaging by analyzing the navigator echoes acquired in time series.

Figure 2:
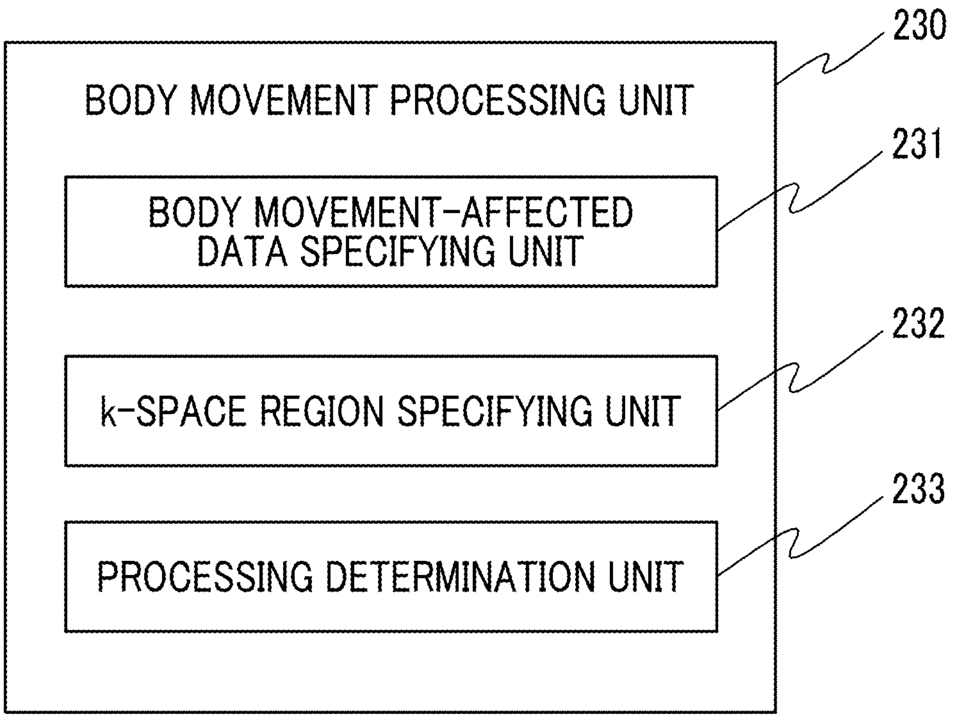
FIG. 2 is a functional block diagram of a processor (body movement processing unit).

The body movement processing unit 230 determines whether or not body movement correction is necessary, whether or not re-measurement is necessary, and the like based on the acquired body movement information. FIG. 2 is a functional block diagram showing functions of the body movement processing unit 230. As shown in FIG. 2, the body movement processing unit 230 may comprise a body movement-affected data specifying unit 231, a k-space region specifying unit 232, and a processing determination unit 233. The body movement-affected data specifying unit 231 determines that the echo signal (measurement data) being measured is data (body movement-affected data) that is being affected by the body movement based on the body movement information during the measurement, for example, the magnitude of the body movement, and specifies the echo signal as the body movement-affected data. The body movement-affected data is a set of one or a plurality of echo signals collected while one body movement occurs, and for example, in a case where the body movement exceeding a predetermined threshold value occurs discontinuously, the body movement-affected data is specified for each body movement.

Figure 3:
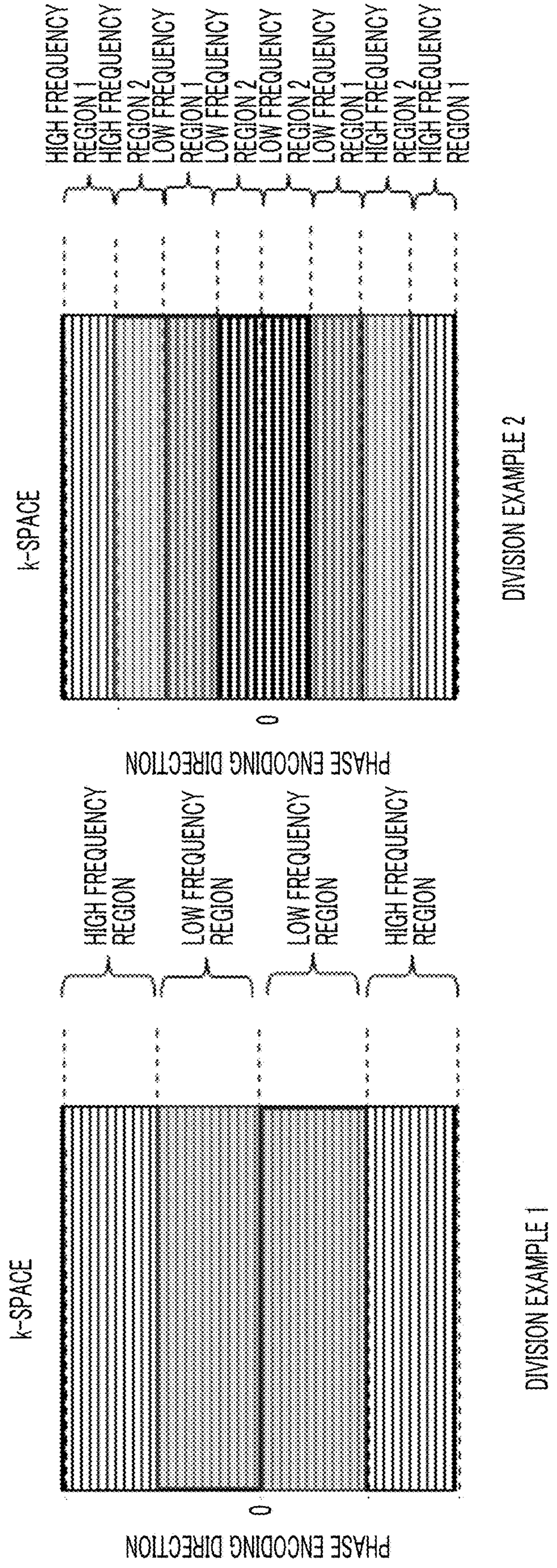
FIG. 3 is a diagram illustrating a region of k-space data.

The k-space region specifying unit 232 divides the k-space data into a plurality of regions in order to specify the position of the body movement-affected data in the k-space by regions of the k-space. The region division is not limited, but may be, for example, as shown in FIG. 3, divided into three regions: a low frequency region on either side of the center of the k-space, and two high frequency regions (upper high frequency region, lower high frequency region) outside the low frequency region, or these may be further divided into two or more regions. In the former case, for example, the low frequency region is set to 50% of the k-space, and each of the two high frequency regions is set to 25% of the k-space. Such region division may be set at a predetermined proportion in advance, or may be set or changed by the user. In a case where the region division is set on the apparatus side, it is possible to estimate in advance using simulation or AI the extent to which image quality deteriorates in a case where data from a certain region is missing, and set the proportion accordingly.

The processing determination unit 233 determines which region the body movement-affected data is in and the continuity of the body movement-affected data (the number of consecutive data points) based on phase encoding information associated with the body movement-affected data according to the region division, and determines whether or not the re-measurement is necessary based on the region and the continuity. In this case, the determination is performed using a threshold value for the continuity. The threshold value may be a predetermined value, or may be a value obtained by adjusting a value set in advance based on the distribution of the body movement-affected data in the k-space. The determination of the continuity of the data using the threshold value and the adjustment thereof will be described in detail in the embodiment described below.

The display controller 250 causes a display device to display the image generated by the image generation unit 220 or accessory information of the image in a predetermined display form. The display controller 250 further performs processing of displaying, on the display device, a GUI for the user to input various conditions or settings related to the operation of the MRI apparatus 1, such as imaging, image generation (including correction), and display, receiving the user settings, and passing the user settings to the related functional unit. The UI unit 30 comprises a display device, an input device, and the like as means for the processor 20 and the user to communicate with each other, and these are connected to the processor 20.

Figure 4:
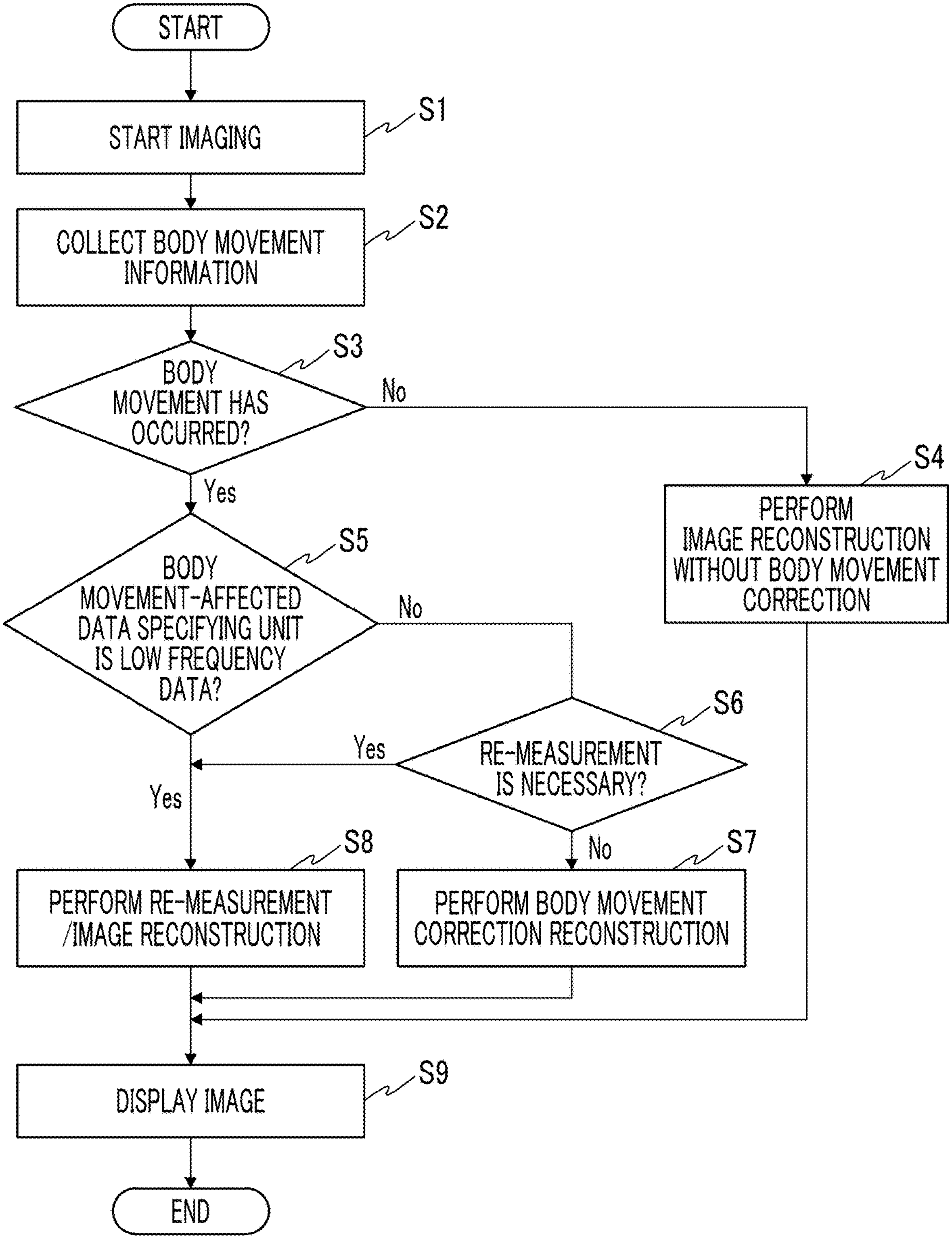
FIG. 4 is a flowchart showing a flow of processing of the processor.

Next, a flow of an imaging operation of the MRI apparatus 1 in the above configuration will be described with reference to FIG. 4.

The subject 50 is placed in the examination space, and imaging is started (S1). Specific conditions for imaging, that is, a pulse sequence and scan parameters (the number of slices, FOV, TE, TR, R factor, and the like) used for imaging are not particularly limited, and imaging is executed by setting various known conditions using known setting methods.

Before or simultaneously with the start of imaging, the body movement processing unit 230 monitors a movement of the subject and collects body movement information (S2). The movement of the subject can be acquired, for example, by collecting navigator echoes for monitoring the movement of the subject separately from the echo signal for image reconstruction, and analyzing a change in a profile obtained by performing Fourier transform on the navigator echoes in a direction of the movement to be monitored or a change in the navigator echoes themselves. Since various sequences are known as a pulse sequence for collecting navigator echoes and an imaging sequence accompanying the pulse sequence, specific description of the sequences will be omitted here.

In addition, instead of using the navigator echo, it is also possible to obtain the movement from a video from a surveillance camera installed in the gantry of the MRI apparatus 1 or in the vicinity of the gantry or a signal of a biological signal monitor worn by the subject, or to use both the video and the signal. The body movement processing unit 230 analyzes the video or the signal and collects body movement information such as the magnitude of the body movement, information regarding a body movement occurrence time, and a type of the body movement. For the acquisition of the movement information using the video of the surveillance camera, a known method can be adopted. For example, a movement vector of each pixel is calculated between frame images of the surveillance camera, and the movement information is acquired using an optical flow calculation or the like. In addition, in a case where a respiratory movement, heart rate, or the like is obtained as a biological signal, it is also possible to use the signal to discriminate the body movement that affects the image, excluding the cyclic movement.

As a result (S3) of the analysis of the body movement processing unit 230, in a case where no body movements that affect the image, such as sudden movements excluding a relatively small periodic movement such as a respiratory movement and heart rate, or positional deviations are detected, and in a case where measurement data (k-space data) necessary for reconstructing the image is collected, the image generation unit 220 performs the image reconstruction using a known image reconstruction method such as Fourier transform or PI calculation using the collected k-space data (S4).

As a result of the analysis of the body movement processing unit 230, in a case where it is determined that the body movement has occurred during the collection of the k-space data (S3), the body movement processing unit 230 (the body movement-affected data specifying unit 231, the k-space region specifying unit 232) specifies measurement data (body movement-affected data) affected by the body movement based on the body movement occurrence time point, and specifies the k-space region thereof. Then, the body movement processing unit 230 (processing determination unit 233) determines whether to perform body movement correction reconfiguration or to perform re-measurement by deleting or correcting the specified body movement-affected data (S5, S6). The determination as to whether or not to perform the re-measurement is performed, for example, based on whether the body movement-affected data is the k-space low frequency data or the k-space high frequency data. The re-measurement is performed in a case of the k-space low frequency data (S5), and the process proceeds to the next determination step (S6) in a case of the k-space high frequency data.

Further, the body movement processing unit 230 determines whether to perform re-measurement based on the position and the continuity of the body movement-affected data in the k-space or to use the body movement-affected data for the body movement correction reconstruction without re-measurement (S6). Using a threshold value set in advance or a threshold value adjusted according to the position in the k-space, in a case where the continuity is equal to or greater than the threshold value, re-measurement is performed, and, in a case where the continuity is less than the threshold value, measurement is continued without re-measurement. Specific determination for each case will be described below.

Figure 5:
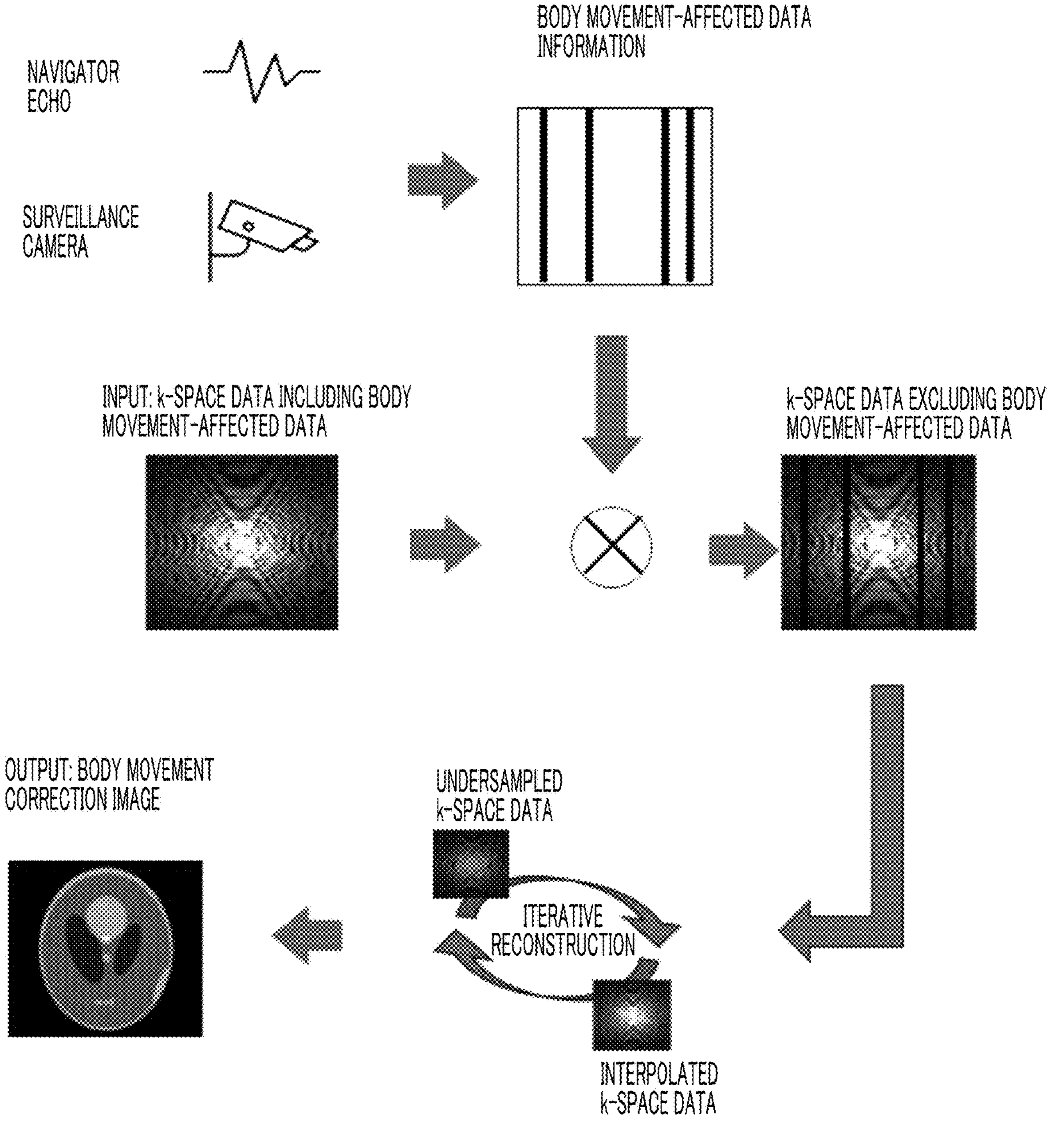
FIG. 5 is a diagram schematically showing sequential reconstruction.

In a case where the body movement correction is performed using the k-space data collected without re-taking the data, the image generation unit 220 generates a body movement correction image using a predetermined method (S7). As a method of the body movement correction, known methods such as zero-filling in which correction target data is deleted and filled with zero, half scan reconstruction, reconstruction in which data estimation is performed using the k-space Hermitian symmetry, and sequential reconstruction using k-space data after zero-filling as shown in FIG. 5 can be adopted.

In a case where it is determined that the body movement correction reconstruction using the body movement-affected data is not possible or it is determined that the re-measurement is necessary, the imaging controller 210 controls the imaging unit 10 to perform the re-measurement. That is, the imaging unit 10 stores the k-space data acquired up until the occurrence of the body movement in the memory and re-measures the k-space data after the time point at which the body movement occurs (S8). In a case where the measurement data necessary for the image reconstruction is collected by the re-measurement, the image generation unit 220 generates an image using the measurement data before the re-measurement stored in the memory and the data collected after the re-measurement (S8). The re-measurement may be automatically performed according to the result of the determination step S6, but the re-measurement may be started upon approval or selection from the user.

The image generated by the image generation unit 220 is displayed on the display device of the UI unit 30 via the display controller 250 (S9). In addition, the image data may be transmitted to an external storage device, a database, or the like.

As described above, the MRI apparatus according to the present embodiment monitors the body movement of the subject during the examination, specifies image-influencing data that is the measurement data acquired in a case where the body movement occurs and that has a large influence of the body movement on the image, and determines whether or not the re-measurement is necessary, based on the position of the image-influencing data in the k-space and the continuity of the data in the k-space. Accordingly, it is possible to reduce the frequency of the re-measurement, prevent the re-measurement of measurement data that does not need to be re-measured originally, and prevent the imaging time from being prolonged.

Hereinafter, a specific embodiment of the processing performed by the body movement processing unit 230 for each of various cases of the body movement occurring during the data collection will be described.

Embodiment 1

In the present embodiment, in a case where there is the body movement-affected data in the low frequency region of the k-space, the re-measurement is performed, and, in a case where there is the body movement-affected data in the high frequency region of the k-space, whether or not the re-measurement is necessary is determined based on the continuity of the body movement-affected data. Hereinafter, the operation of the processing determination unit 233 of the present embodiment will be described again with reference to the flowchart of FIG. 4. In the present embodiment, a case will be described in which the sampling order is a sequential order in which the sampling is performed from a high frequency region on one side of the k-space through a low frequency region to a high frequency region on the other side of the k-space.

In the present embodiment, first, the processing determination unit 233 determines in which region of the k-space the body movement-affected data specified by the body movement-affected data specifying unit 231 is located (S5). It is assumed that the region of the k-space is divided into a high frequency region and a low frequency region, for example, as shown in Division Example 1 of FIG. 3. In this determination, in a case where the body movement-affected data is low frequency data, the low frequency data is re-taken. That is, as shown in FIG. 6, the re-measurement is started from the phase encoding step that is recognized as the body movement-affected data of the low frequency data, and thereafter the subsequent phase encoding data, that is, the data from the low frequency region to the high frequency region that have not been previously measured are measured.

Figure 6:
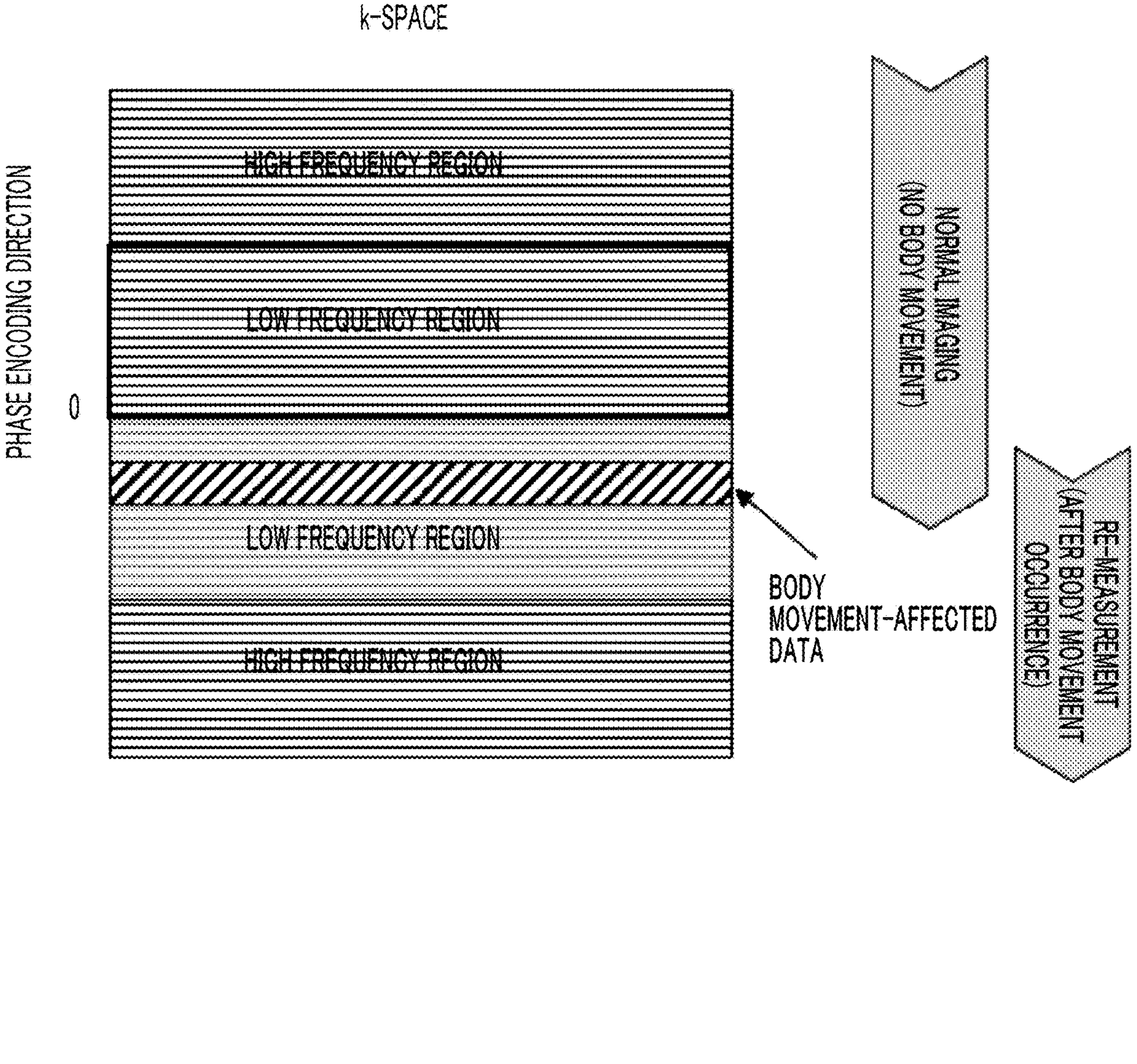
FIG. 6 is a diagram illustrating re-taking of measurement data.

In the example shown in FIG. 6, the body movement-affected data is present only in the low frequency region, but the re-taking is performed in the same manner even in a case where the body movement-affected data is present from the high frequency region to the low frequency region. That is, in a case where the body movement-affected data is present in the low frequency region, it is determined that the re-measurement is necessary in the determination step (S5, S6).

Figure 7:
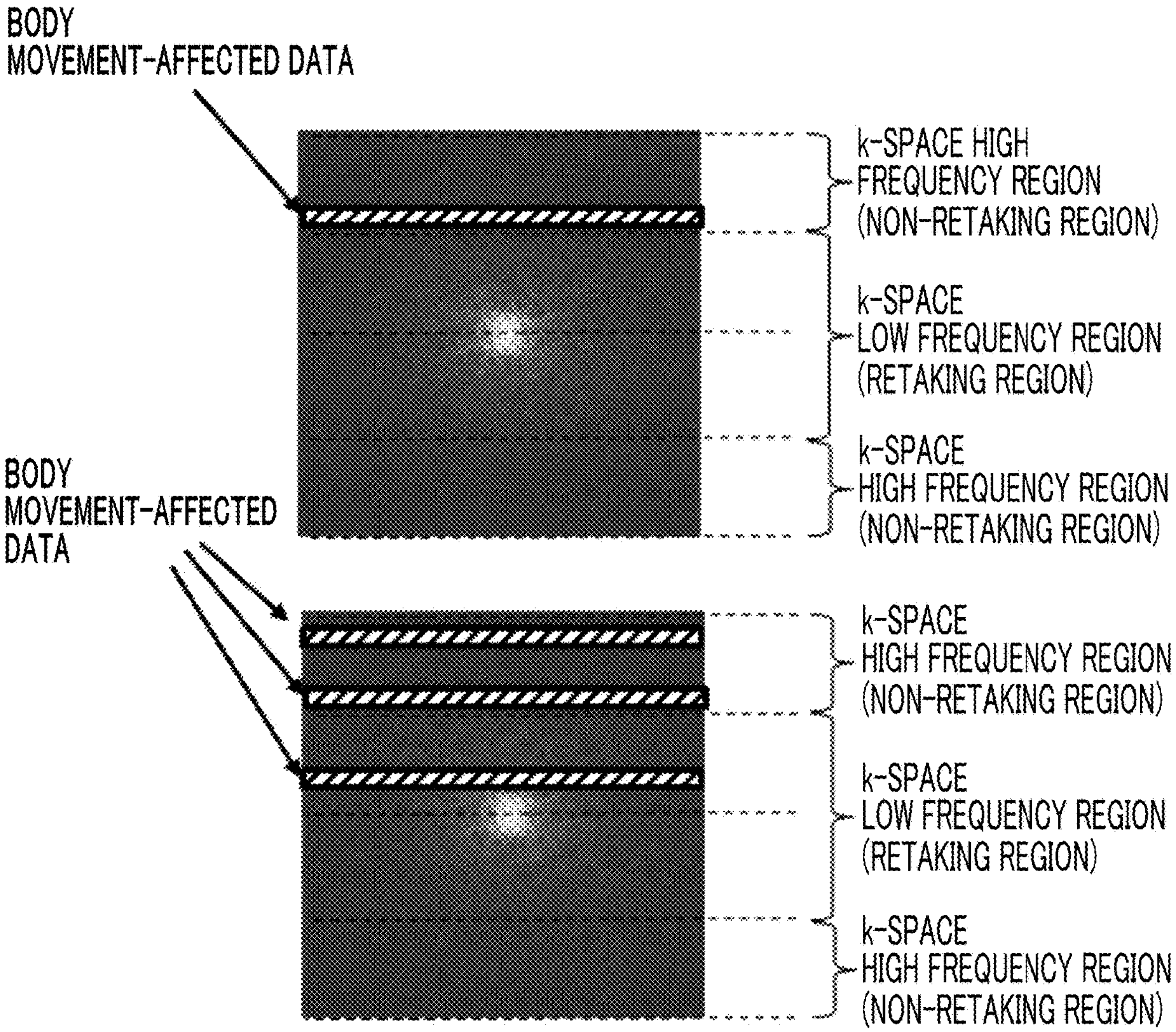
FIG. 7 is a diagram showing two examples of body movement-affected data generated during k-space data measurement.

On the other hand, as shown on the upper side of FIG. 7, in a case where the body movement-affected data is the high frequency data, whether or not re-taking is necessary is further determined based on the number of data points of the high frequency data and the number of consecutive data points (S6). In the second determination, a predetermined threshold value TH is set for the number of consecutive data points. In a case where the number of consecutive data points is equal to or greater than TH, the body movement-affected data is re-taken, and, in a case where the number of consecutive data points is less than TH, the re-taking is not performed. The number of consecutive data points means the number of data points that are consecutive on the k-space in a case where the measurement data is arranged in the k-space. In a case of the sequential order, the measurement order directly maps onto the arrangement order in the k-space, which can be either from the high frequency region toward the low frequency region or from the low frequency region toward the high frequency region.

Here, the body movement-affected data means a set of data specified in response to one body movement, and, in a case where the body movements occur a plurality of times non-consecutively from the measurement of the echo to the body movement analysis, a plurality of body movement-affected data may be present as shown on the lower side of FIG. 7. In this case, for one or a plurality of body movement-affected data generated within a time interval (monitoring window) in which the body movement is monitored, the body movement processing unit 230 determines whether the number of consecutive data points is equal to or greater than a threshold value or is less than the threshold value.

The fact that the number is equal to or greater than the threshold value means that, for example, there are consecutive data points that cannot be used in a case of performing the body movement correction reconstruction. For example, even in a case where the body movement-affected data are zero-filled or estimated via sequential calculations for reconstruction, the image quality deteriorates due to the paucity of information in that region. Therefore, in the second determination step, in order to prevent such deterioration of the image, it is determined that the re-taking (re-measurement) is necessary in a case where the number of consecutive data points is equal to or greater than the threshold value.

In this case, the processing determination unit 233 may adjust the threshold value used in the second determination step S6 according to the position of the body movement-affected data in the k-space. For example, in the example on the lower side of FIG. 7 where a plurality of body movement-affected data are specified, different threshold values are applied to the number of consecutive data points for the body movement-affected data located toward the high frequency side and the body movement-affected data located closer to the low frequency side, with the threshold value for the former being made larger than the threshold value for the latter, that is, the closer to the low frequency side, the threshold value is made smaller, so that even a small number of consecutive data points requires the re-taking.

Figure 8:
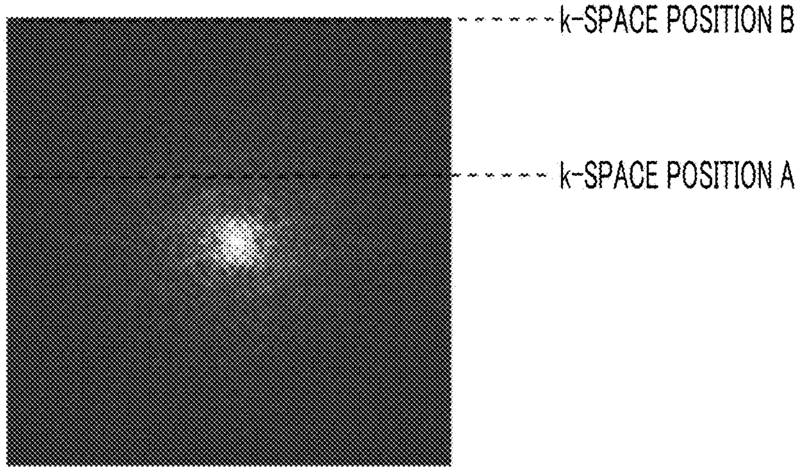
FIG. 8 is a diagram illustrating a threshold value related to continuity of the body movement-affected data.
Figure 8:
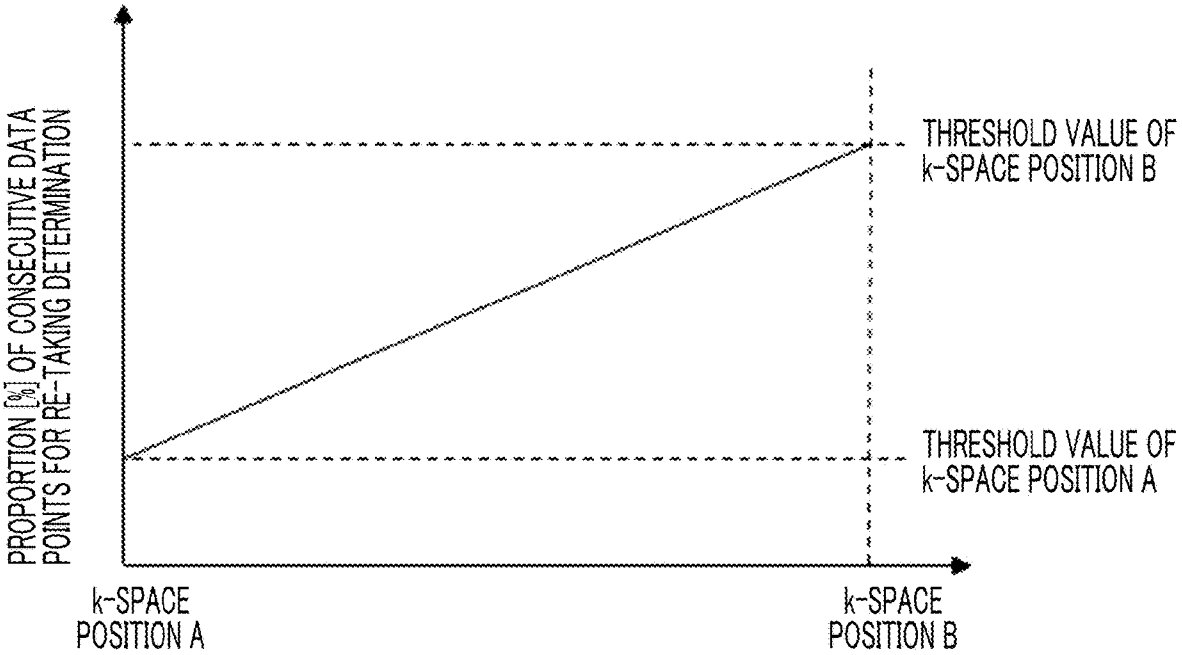

In a case where the high frequency region is finely divided as shown in Division Example 2 of FIG. 3, the threshold value may be changed in a stepwise manner for each region. Alternatively, as shown in FIG. 8, the phase encoding amount is changed linearly (linear function) or non-linearly (exponential function or the like). That is, in a case where the proportion of the consecutive data points for re-taking determination at the k-space position (simply referred to as k-space position) in the phase direction is measured from the low frequency region to the high frequency region, the proportion is represented by the following equation.

[Proportion (%) of consecutive data points for re-taking determination]=[(threshold value of *k*-space position *B*−threshold value of *k*-space position *A*)/(*k*-space position *B*−*k*-space position *A*)]×(*k*-space position at the time of body movement occurrence)

In a case where the proportion is measured from the high frequency region to the low frequency region, the "k-space position in the time of body movement occurrence" is set as "k-space position at the time of body movement end". That is, the proportion of the consecutive data points determined by the threshold value is determined with reference to the position of the data in the lowest frequency region of the body movement-affected data.

In this way, by increasing the threshold value for determining the continuity of the body movement-affected data as the body movement-affected data is farther from the low frequency region, a stricter threshold value (smaller threshold value) is used to determine whether or not to re-take the body movement-affected data that includes data in the region close to the low frequency region, thereby preventing the loss of information on data that affects the contrast of the image. In addition, for the body movement-affected data composed of data on the higher frequency side, because their impact on the image is small, body movement correction is executed and re-taking is not executed, thereby preventing extension in imaging time.

The adjustment of the threshold value based on the position of the body movement-affected data is not essential, but the extension in imaging time can be reduced while maintaining the image quality by adjusting the threshold value according to the position of the body movement-affected data in the k-space.

According to the present embodiment, in a case where the body movement-affected data is present in the high frequency region of the k-space, whether or not the re-measurement is necessary is determined based on the continuity of the body movement-affected data, thereby minimizing the frequency of the re-measurement or the amount of data to be remeasured.

In the above-described embodiment, in a case where the body movement-affected data is present in the low frequency region, it is determined that the re-measurement is necessary, but it is also possible to set a threshold value for the number of consecutive data points of the body movement-affected data in the low frequency region that is smaller than that in the high frequency region, and not to perform the re-taking. In this case, a gradient may also be provided for the threshold value in the low frequency region, so that the threshold value is set lower as the value approaches 0 encoding.

Embodiment 2

Figure 9:
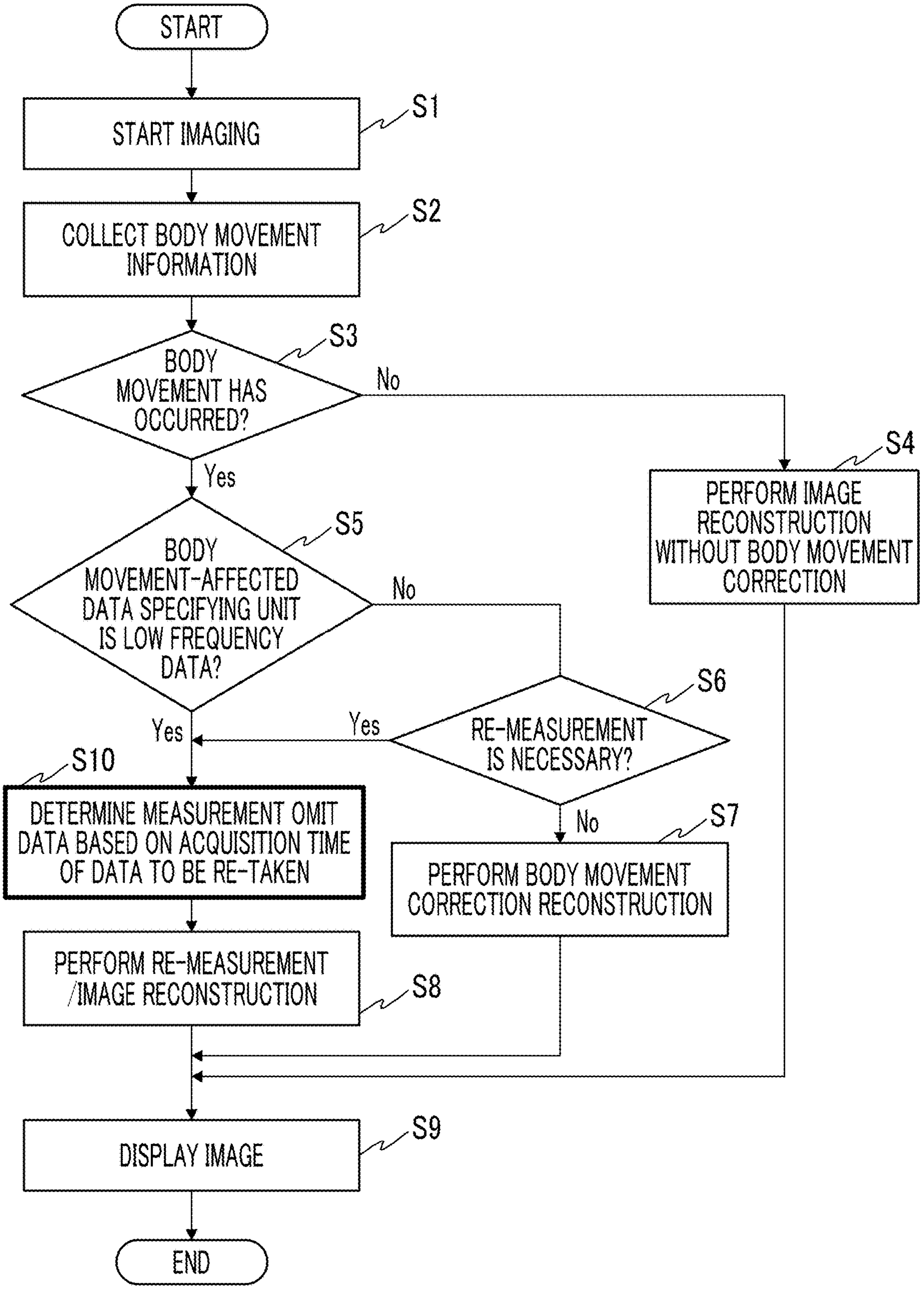
FIG. 9 is a flowchart showing a flow of processing of a processor of Embodiment 2.

In the present embodiment, in a case where the body movement-affected data is in the low frequency region of the k-space and the low frequency data is re-taken, the measurement data to be re-measured is limited, thereby reducing the extension in measurement time including the re-measurement. A flow of processing of the body movement processing unit 230 of the present embodiment will be described with reference to FIG. 9. In FIG. 9, the same processes as that in FIG. 4 are denoted by the same reference numerals, and redundant description will be omitted.

Figure 10:
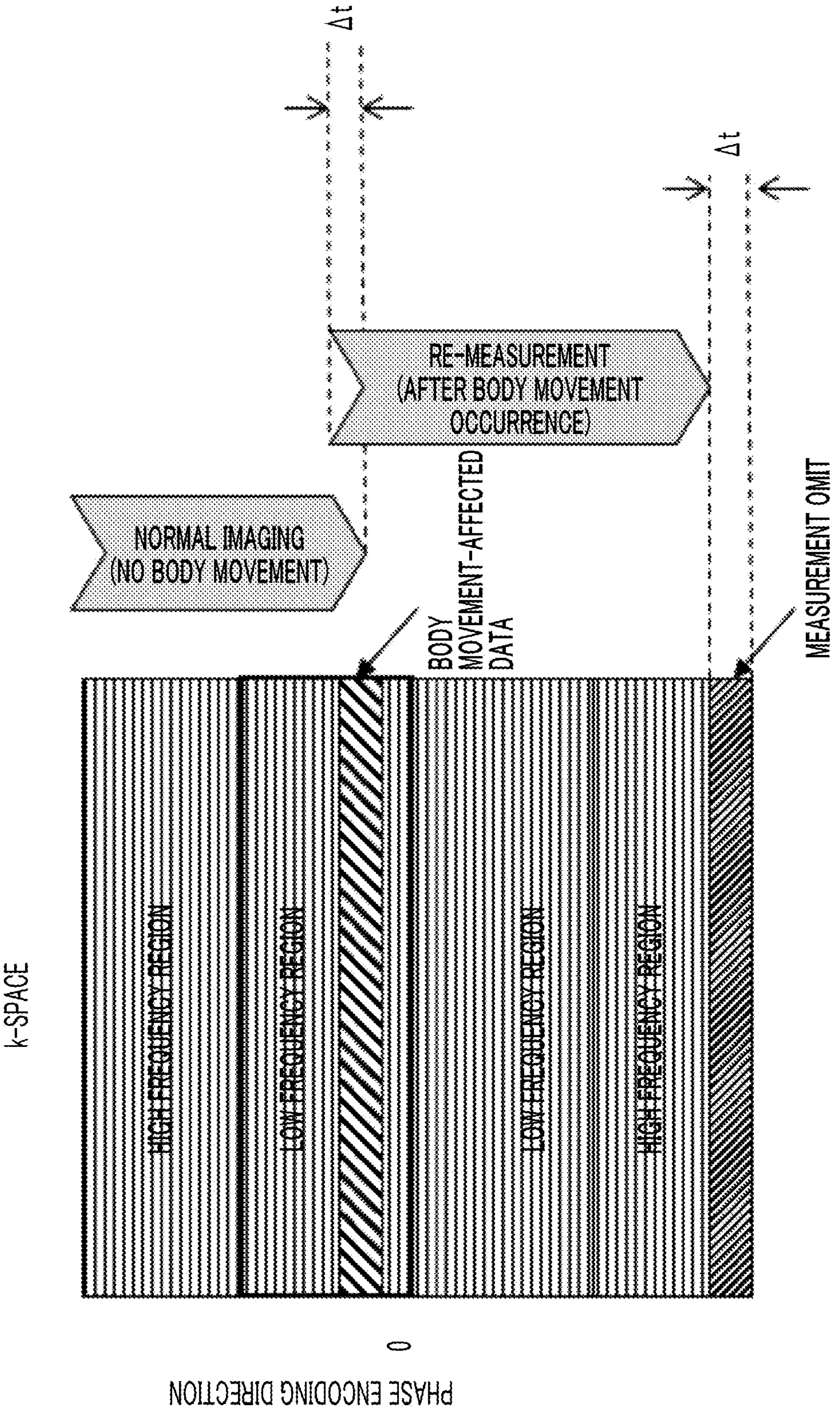
FIG. 10 is a diagram illustrating the processing of Embodiment 2.

Here, FIG. 10 shows an example of a case to which the present embodiment is applied. Here, the sampling order is described taking the case of the sequential ordering as an example in the same manner as in Embodiment 1, but is not limited to this. As shown in FIG. 10, a case where a body movement occurs during the measurement of the low frequency data is assumed in a case where the measurement (scanning) is performed in order from a high frequency region on one side of the k-space through the origin to a high frequency region on the other side of the k-space. The body movement processing unit 230 determines whether the data measured during the body movement is the body movement-affected data based on the part in which the body movement has occurred or the magnitude of the body movement (S3), and, in a case where the data is the body movement-affected data, the body movement processing unit 230 determines to which region of the k-space the data belongs (S5). In a case where the body movement-affected data is the low frequency data, the re-measurement is performed. In the re-measurement, the remaining data (part of the low frequency data) excluding the high frequency data that has already been measured and the low frequency data measured in a case where no body movement occurs, and the unmeasured high frequency data are measured among the k-space data.

In this case, the processing determination unit 233 omits the acquisition of the high frequency data for a period equivalent to an acquisition period (Δt) of the body movement-affected data to be re-taken (S10). That is, the remaining high frequency data is measured by omitting the phase encoding steps whose number is approximately the same as the number of phase encoding steps of the low frequency data to be re-measured. It is preferable that the high frequency data to be omitted is data positioned on the highest frequency side. Alternatively, the phase encoding steps may be omitted in a distributed manner, and the high frequency data may be thinned out and measured.

The number of phase encoding steps for which the measurement is omitted may be the same as, less than, or greater than the number of phase encoding steps of the low frequency data, as long as body movement correction is possible even though the measurement is omitted, and the time extension due to the re-measurement can be compensated and the measurement time can be shortened by omitting the measurement as much as possible within a possible range.

Finally, in a case where all the k-space data are collected, the image reconstruction or the body movement correction reconstruction (S8) using the k-space data is the same as that in Embodiment 1.

According to the present embodiment, in a case where the re-measurement is necessary, the time related to the re-measurement of the body movement-affected data to be re-measured can be canceled by omitting the measurement of a part of the high frequency data, and it is possible to prevent the extension in measurement time including the re-measurement.

In FIG. 10, a case where the low frequency data is re-measured is illustrated, but the present embodiment can also be applied to a case where the high frequency data is re-taken before the low frequency data is measured. That is, the number of phase encoding steps that is approximately the same as the number of phase encoding steps of the high frequency data to be re-taken may be omitted in a case where the unmeasured high frequency data is measured.

As described above, the embodiments of the processing performed by the body movement processing unit of the MRI apparatus according to the embodiment of the present invention have been described. However, the present invention is characterized in that the processing determination and the subsequent re-measurement are controlled in consideration of the continuity of the body movement-affected data, and the present invention is not limited to these embodiments and can be modified in accordance with various aspects in which the body movement occurs.

EXPLANATION OF REFERENCES

10: imaging unit
20: processor
210: imaging controller
220: image generation unit
230: body movement processing unit
231: body movement-affected data specifying unit
232: k-space region specifying unit
233: processing determination unit
250: display controller

What is claimed is:

1. A magnetic resonance imaging apparatus comprising:

an imaging unit that collects nuclear magnetic resonance signals of a subject;

an image generation unit that reconstructs an image of the subject using k-space data consisting of the nuclear magnetic resonance signals collected by the imaging unit;

a body movement processing unit that analyzes a body movement of the subject during imaging and that specifies body movement-affected data that is affected by the body movement of the subject among the k-space data; and a processor that controls the imaging unit and the image generation unit, wherein the processor determines whether to subject the body movement-affected data to body movement correction reconstruction or to re-measure the body movement-affected data according to a position of the body movement-affected data in a k-space and a number of data points being consecutive in a data arrangement direction of the k-space of the body movement-affected data, and, in a case where it is determined to re-measure at least a part of the body movement-affected data, the processor controls a way by which re-measurement is executed by the imaging unit.

2. The magnetic resonance imaging apparatus according to claim 1, wherein the processor divides the k-space into at least two regions including a low frequency region and a high frequency region, controls the imaging unit to execute the re-measurement regardless of the number of consecutive data points in a case where all of the body movement-affected data are low frequency region data, and determines whether or not the re-measurement is necessary based on a threshold value set for the number of consecutive data points in a case where the body movement-affected data are high frequency region data.

3. The magnetic resonance imaging apparatus according to claim 1, wherein, in a case where the number of consecutive data points of the body movement-affected data is equal to or greater than a preset threshold value, the processor controls the imaging unit to execute the re-measurement of the body movement-affected data regardless of a position of the consecutively collected data in the k-space.

4. The magnetic resonance imaging apparatus according to claim 3, wherein the processor sets the threshold value to a different value for each region of the k-space divided into a plurality of regions, and the processor determines whether or not the re-measurement is necessary, by using the threshold value set for the region of the k-space to which the consecutively collected data belong.

5. The magnetic resonance imaging apparatus according to claim 3, wherein the processor uses, as the threshold value, a threshold value that changes from a low frequency region to a high frequency region of the k-space, and determines whether or not the re-measurement is necessary, by using a threshold value according to the position of the consecutively collected data in the k-space.

6. The magnetic resonance imaging apparatus according to claim 1, wherein, in a case where the number of consecutive data points of the body movement-affected data is less than a preset threshold value, the processor determines that the re-measurement of the body movement-affected data is not necessary, and the image generation unit performs the body movement correction reconstruction by correcting or excluding the body movement-affected data and generates an image.

7. The magnetic resonance imaging apparatus according to claim 1, wherein, in a case of re-measuring at least a part of the body movement-affected data and unmeasured data, the processor controls the imaging unit to omit measurement of at least a part of the unmeasured data.

8. The magnetic resonance imaging apparatus according to claim 7, wherein the processor sets the number of data points of the unmeasured data for which the measurement is omitted to be equal to the number of data points of the body movement-affected data.

9. The magnetic resonance imaging apparatus according to claim 7, wherein the processor controls the imaging unit to perform measurement by thinning out the unmeasured data.

10. A method of controlling a magnetic resonance imaging apparatus, the method comprising:

a step of specifying body movement-affected data affected by a body movement, which is included in k-space data collected by the magnetic resonance imaging apparatus;

a step of determining whether or not re-measurement of the body movement-affected data is necessary, based on a position of the body movement-affected data in a k-space;

a step of, in a case where it is determined that the re-measurement is not necessary, further determining whether or not re-measurement of the body movement-affected data is necessary, based on a number of data points being consecutive in a data arrangement direction of the k-space of the body movement-affected data; and a step of, in a case where it is determined that re-measurement of at least a part of the body movement-affected data is necessary, setting a condition for the re-measurement.

11. The method of controlling a magnetic resonance imaging apparatus according to claim 10, wherein, in the step of setting the condition for the re-measurement, in a case where the re-measurement includes measurement of unmeasured data in the k-space data, a condition for omitting measurement of a part of the unmeasured data is set.

* * * * *